United States Patent [19]

Boden et al.

[11] Patent Number: 4,528,402

[45] Date of Patent: * Jul. 9, 1985

[54] HYDROCARBYLOXY ALKANAL

[75] Inventors: Richard M. Boden, Ocean; William L. Schreiber, Jackson; Futoshi Fujioka, Wanamassa, all of N.J.; Patrick Chant, Brooklyn, N.Y.; Lambert Dekker, Wyckoff, N.J.

[73] Assignee: International Flavors & Fragrances Inc., New York, N.Y.

[*] Notice: The portion of the term of this patent subsequent to Apr. 17, 2001 has been disclaimed.

[21] Appl. No.: 535,931

[22] Filed: Sep. 26, 1983

Related U.S. Application Data

[62] Division of Ser. No. 366,079, Apr. 6, 1982, Pat. No. 4,443,633.

[51] Int. Cl.$^3$ ................................. C07C 47/115
[52] U.S. Cl. ................................. 568/445
[58] Field of Search ................. 568/445, 665, 444

[56] References Cited

U.S. PATENT DOCUMENTS 2,388,765 11/1945 Rummelsburg .............. 568/665
3,028,419 4/1962 Bloch .............................. 568/444
4,443,633 4/1984 Boden et al. ................. 568/445

Primary Examiner—Bernard Helfin
Attorney, Agent, or Firm—Arthur L. Liberman

[57] ABSTRACT

Described are hydrocarbyloxy alkanals defined according to the generic structure:

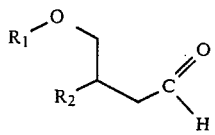

wherein $R_1$ represents one of the moieties:

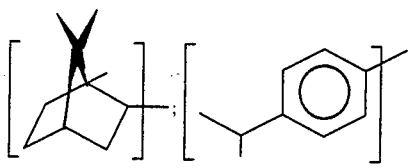

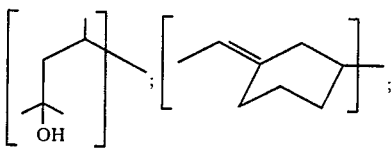

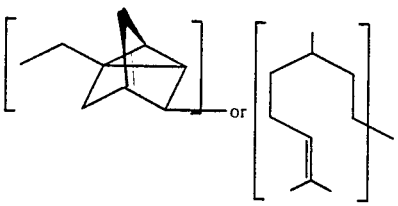

and $R_2$ represents hydrogen or methyl prepared according to the process of first reacting an allyl alcohol defined according to the structure:

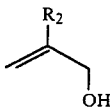

with a hydrocarbon or hydrocarbyl halide defined according to the structure:

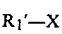

having an electrophilic center wherein $R_1'$ is saturated or unsaturated hydrocarbyl and X represents halogen or hydrogen with the provisos that:

$R_1'$ is saturated hydrocarbyl when X is halogen and
$R_1'$ is unsaturated hydrocarbyl when X is hydrogen.

Also described are organoleptic uses of such hydrocarbyloxy alkanals in the field of perfumery, colognes and perfumed articles (e.g. perfumed plastics, solid or liquid anionic, cationic, nonionic or zwitterionic detergents, fabric softener compositions or drier-added fabric softener articles).

1 Claim, 15 Drawing Figures

FIG. I

GLC PROFILE FOR EXAMPLE I.

GLC PROFILE FOR EXAMPLE I.

GLC PROFILE FOR EXAMPLE I.

GLC PROFILE FOR EXAMPLE II.

GLC PROFILE FOR FRACTION I OF EXAMPLE II.

GLC PROFILE FOR FRACTION 4 OF EXAMPLE II.

GLC PROFILE FOR FRACTION 7 OF EXAMPLE II.

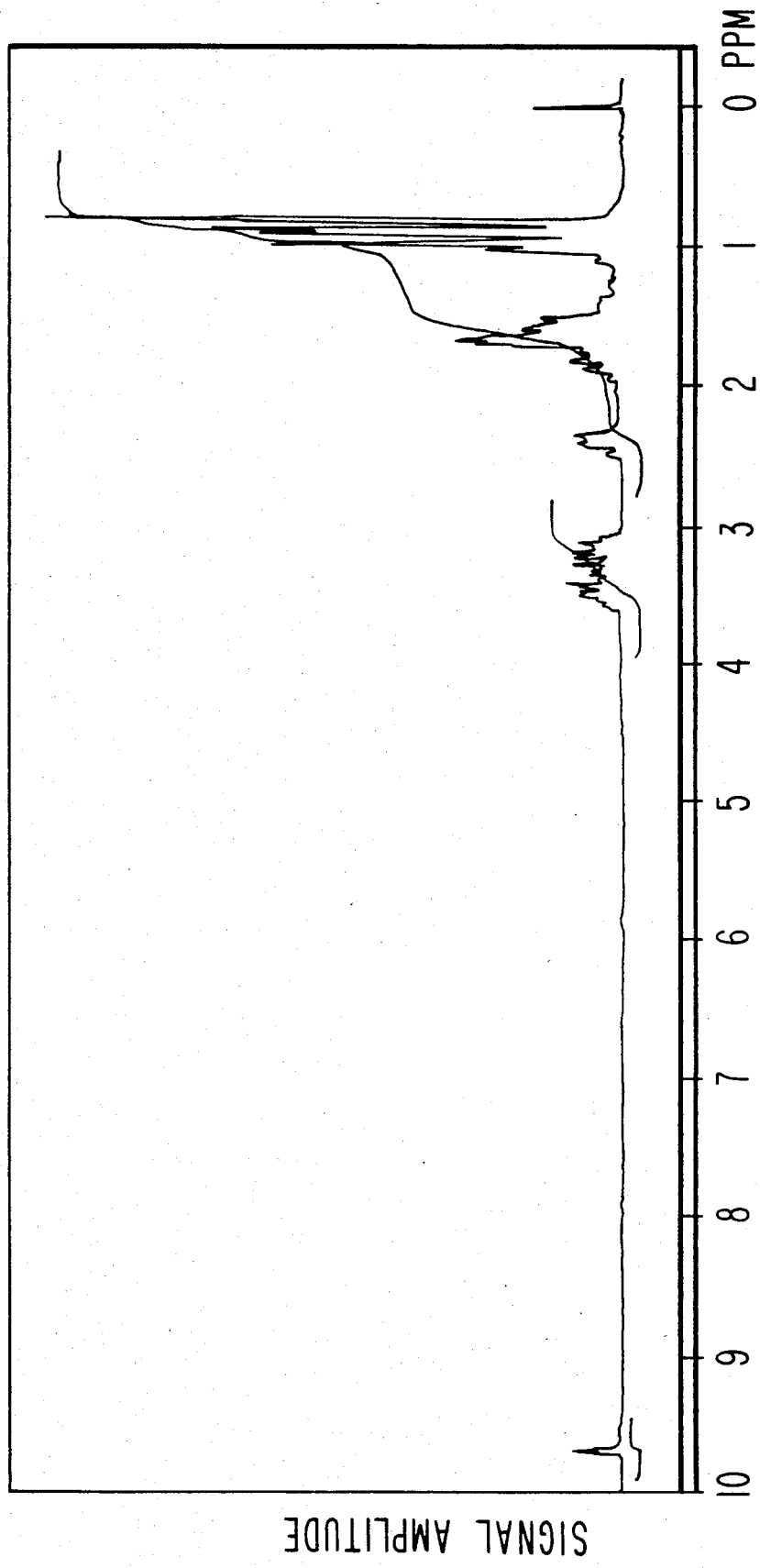

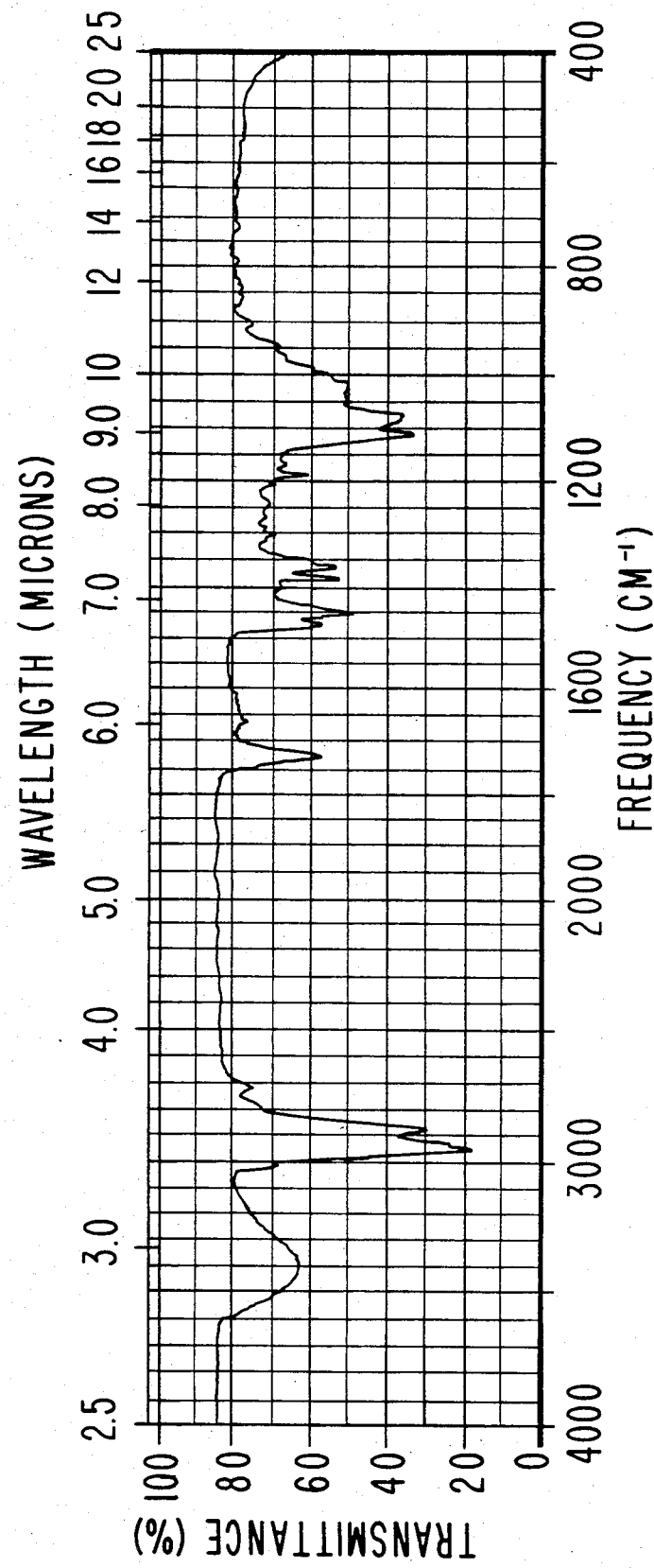

HYDROCARBYLOXY ALKANAL

This is a divisional of application Ser. No. 366,079, filed Apr. 6, 1982, and now U.S. Pat. No. 4,443,633.

BACKGROUND OF THE INVENTION

The instant invention relates to norbornyloxy butanal defined according to the structure:

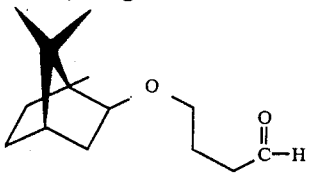

as well as a novel process for preparing such a hydrocarbyloxy alkanal by first reacting camphene having the structure:

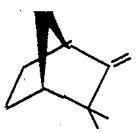

with allyl alcohol having the structure:

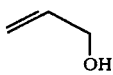

in order to form norbornyl allyl ether having the structure:

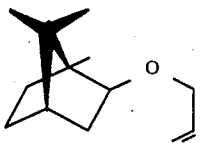

and then reacting the resulting norbornyl allyl ether via an oxo reaction using carbon monoxide and oxygen to form the compound having the structure:

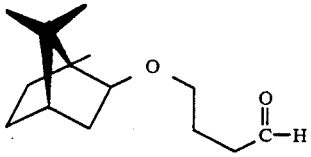

Inexpensive chemical compounds which can provide natural pine, cypress-like and fir-balsam-like aroma nuances are highly desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

There is, accordingly, a continuing effort to find synthetic materials which will provide, enhance or augment the fragrance notes provided by natural essential oils or compositions thereof. Unfortunately, many of the synthetic materials either have the desired nuances only to a relatively small degree or they contribute undesirable or unwanted odor to perfume compositions, perfumed articles and colognes.

Norbornyl oxyacetaldehydes have been previously made the subject of application for U.S. Letters Patent Ser. No. 303,012 filed on Sept. 17, 1981. This compound has the structure:

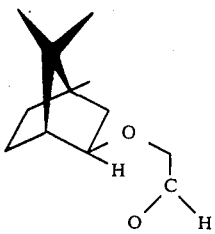

and it is disclosed in said application for U.S. Letters Patent Ser. No. 303,012 filed on Sept. 17, 1981 that the compound has intense and long-lasting woody, lavender-like, rosemary-like, green aromas with rosemary-like, lavandin-like, woody and natural pine oil-like and fresh herbaceous nuances on dry-out.

The compound of the instant invention defined according to the structure:

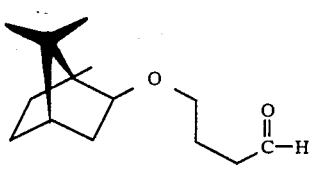

has properties in the perfumery field which are unexpectedly, unobviously and advantageously superior over the properties of the product having the structure:

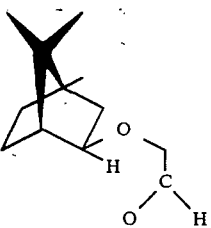

Furthermore, although norbornyl derivatives are known in the art for producing piney aromas such as, for example, those disclosed in U.S. Pat. No. 4,153,811 issued on May 8, 1979, the inexpensive norbornyl oxybutyraldehyde type of compound has heretofore been unknown.

Thus U.S. Pat. No. 4,153,811 discloses the use of substituted norbornane derivatives of the genus of compounds having the structure:

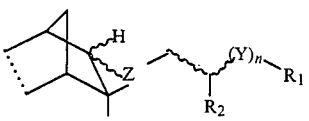

wherein each of the dashed lines represents a carbon-carbon single bond or a carbon-carbon double bond with the proviso that at least one of the dashed lines is a carbon-carbon single bond; wherein n is 0 or 1 with the proviso that n is 1 when both dashed lines are carbon-carbon single bonds and n is 0 when one of the dashed lines is a carbon-carbon double bond; wherein $R_1$ and $R_2$ are each the same or different hydrogen or lower alkyl; wherein Y is:

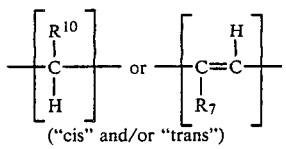

("cis" and/or "trans")

wherein Z is one of the moieties:

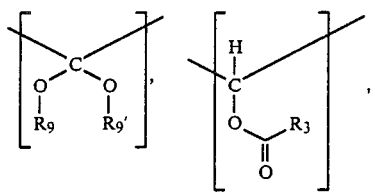

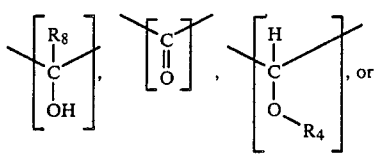

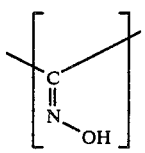

wherein $R_3$ and $R_4$ are each alkyl; wherein $R_7$, $R_8$ and $R_{10}$ are each the same or different hydrogen or lower alkyl; wherein $R_9$ and $R_9'$ taken separately are the same or different lower alkyl, or taken together is lower alkylene; wherein the dotted line represents a carbon-carbon single bond or a carbon-carbon double bond; and wherein each of the wavy lines represents, in the alternative, exo or endo isomers.

U.S. Pat. No. 3,852,358 issued on Dec. 3, 1974 discloses a process for producing 2-acetyl-3,3-dimethyl-5-norbornene in both the exo and endo forms which have uses in perfumery and other fragrance applications. These compounds have the structures:

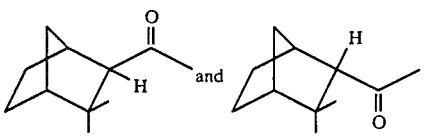

These compounds, produced by reaction of cyclopentadiene with mesityl oxide, are starting materials for producing a number of the compound of our invention. However, the compound of our invention has unexpected, unobvious and advantageous properties when compared with the 2-acetyl-3,3-dimethyl-5-norbornene of U.S. Pat. No. 3,852,358.

U.S. Pat. No. 3,942,761 discloses the use in perfumery of 4-(2'-norbornyl)-2-butanones having the structure:

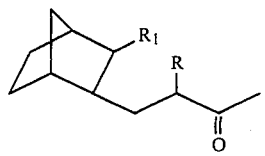

wherein $R_1$ is hydrogen or methyl and R is hydrogen or lower alkyl containing from 1 to 8 carbon atoms. Such compounds have structures which are different in kind from the structures of the compounds of our invention. Also disclosed as intermediates for producing the foregoing compounds are compounds having the generic structure:

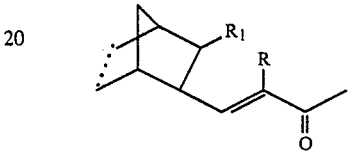

wherein the dotted line is a carbon-carbon single bond or a carbon-carbon double bond. In addition, the following reaction sequence is set forth therein:

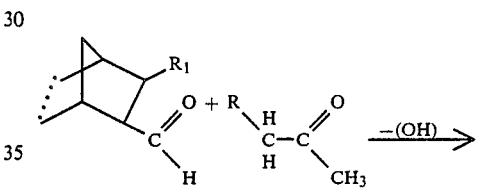

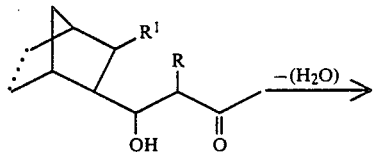

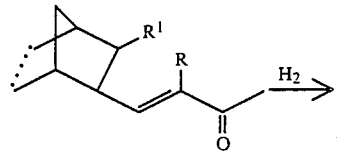

Arctander, "Perfume and Flavor Chemicals", 1969, Vol. 1, discloses the use in perfume compositions and in foodstuff flavors of "fenchone", "fenchyl alcohol", "camphene carbinol", and "camphene carbinyl acetate", thus:

(i) "1385: FENCHONE laevo-Fenchone (dextro- is known but less common as a fragrance material). 1,3,3-trimethyl-2-norbornanone. 1,3,3-trimethyl bicyclo-1,2,2-heptanone-2.

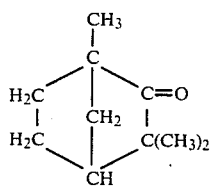

Warm-camphoraceous, powerful and diffusive, basically sweet odor. Warm, somewhat burning and bitter taste with a medicinal note. This ketone finds some use as a masking odor in industrial fragrances. It is also used in the reconstruction of fennel oil and a few other essential oils. In spite of its rather unpleasant taste, it is used in various berry complex flavors, in spice complexes and in certain types of liquor flavoring. The concentration used is about 0.1 to 5 ppm in the finished product."

(ii) "1387: FENCHYL ALCOHOL 1,3,3-trimethyl-2-norbornanol. 1,3,3-trimethyl bicyclo-1,2,2-heptanol-2. 2-fenchanol. Fenchol.

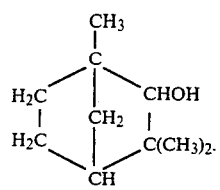

The racemic alpha-fenchol has a somewhat lower melting point, and the beta-fenchols are all liquid at room temperature. Fenchol made by reduction of fenchone from cedarleaf oil is usually a mixture of several isomers, including the crystalline alpha-isomers. The beta-isomer forms a crystalline hydrate which may be sold at room temperature. Almost insoluble in water, soluble in alcohol, miscible with oils. Powerful and diffusive, camphor-like but sweeter and more citrus-like almost lime-like color with more or less of an earthy-dry character, according to the composition and isomer-ratio. The taste is somewhat bitter-lime-like, camphoraceous and slightly woody-musty. This interesting alcohol (or mixed alcohols) finds use in perfume compositions ranging from woody or herbaceous to citrus-lime and even certain floral types. It produces power and "lift" to floral fragrances, and solid background to lime and other citrus bases, having the advantage over the terpenes in being very stable in soap. Fenchyl alcohol is also used in flavor compositions such as strawberry and other berries, lime and spice, etc. The concentration is normally low, e.g. 0.2 up to 5 ppm in the finished product."

(iii) "1028: 3,3-DIMETHYL-$\Delta^2$, beta-NORBORNANE-2-ETHANOL. "Camphene carbinol".

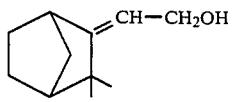

Sweet, camphoraceous, warm and soft odor with a woody undertone. Upon standing it may develop an odor resembling that of celluloid.

Although rarely offered commercially, this chemical could find some use in perfume compositions of the woody, oriental and orissy type, in new variations of pine fragrances, and in various soap and detergent perfumes".

(iv) "1029: 3,3-DIMETHYL-$\Delta^2$-beta-NORBORNANE-2-ETHYLACETATE "Camphene carbinyl acetate".

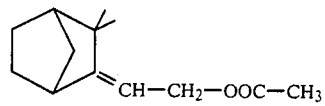

Mild and sweet-woody odor with a floral-piney undertone. The commercial products are probably not well-defined single chemicals, and great variations in odor have been observed.

This ester has been developed in line with the research on sandalwood type odors. The parent alcohol "camphene carbinol" was once considered useful as a sandalwood type material, but it has found more use as a sweetening and enriching ingredient in sophisticated pine fragrances. The title ester finds limited use in perfume compositions of woody character, fougeres, pine fragrances, etc. and it blends very well with the cyclohexanol derivatives, ionones, isobornylacetate, nitromusks, etc.".

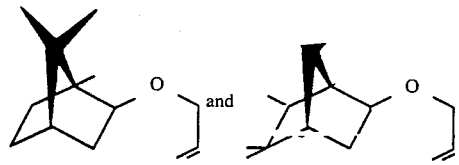

Figure 2:
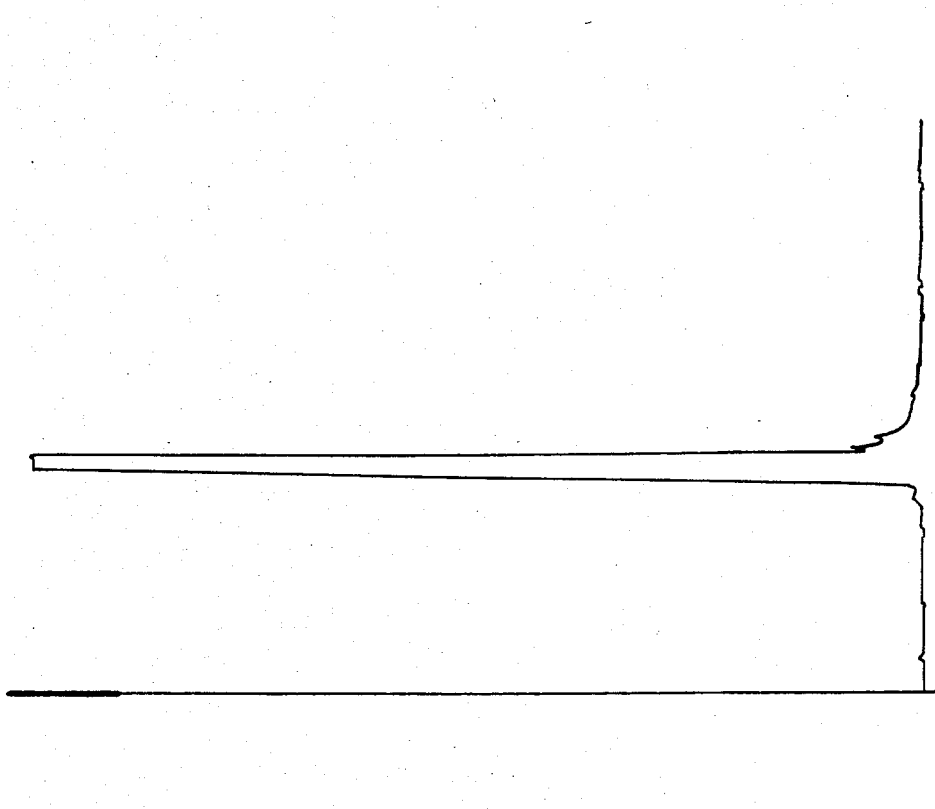

FIG. 2 is the GLC profile for fraction 7 of the redistillation product of the reaction product of Example I containing the compound having the structure:

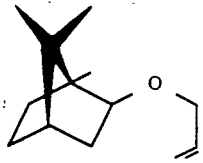

Figure 3:
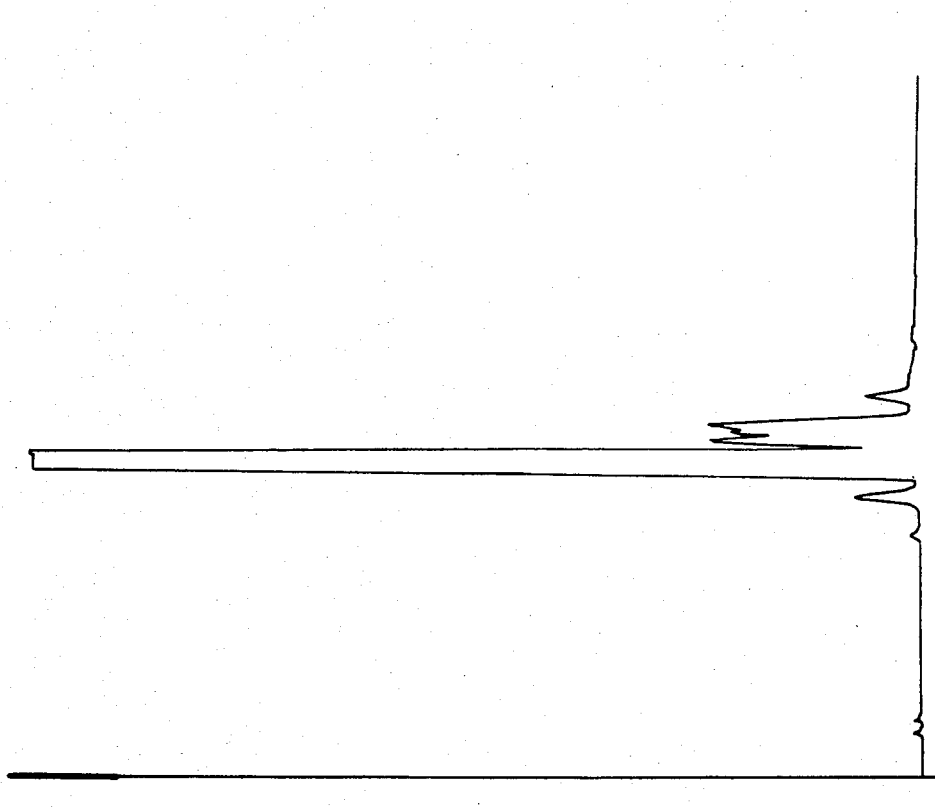

FIG. 3 is the GLC profile for the redistillation product (bulked fractions 2-7) of the reaction product of Example I containing the compound having the structure:

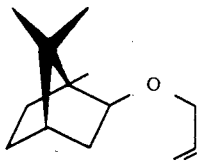

Figure 4:
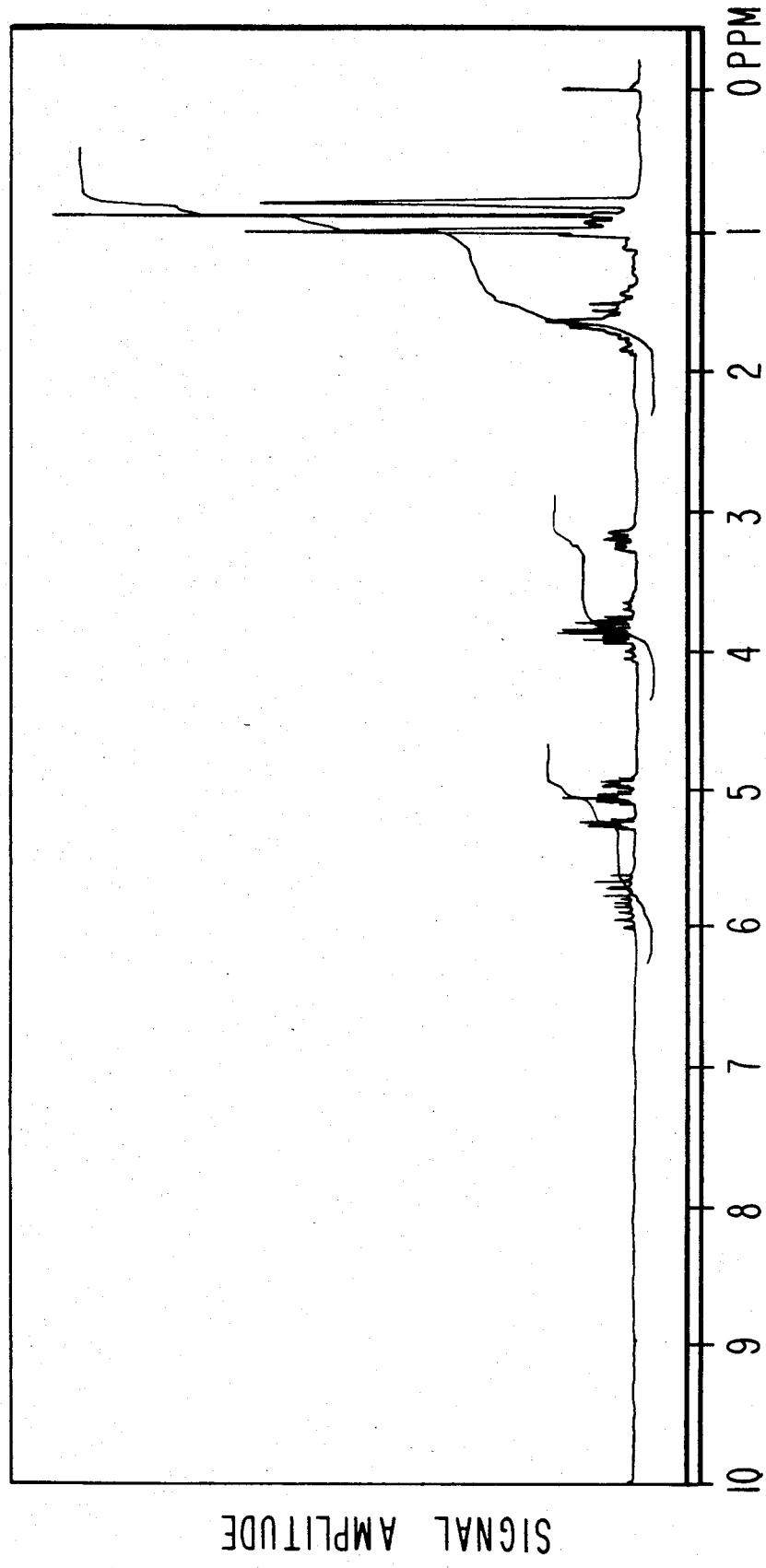

FIG. 4 is the NMR spectrum for bulked fractions 2-7 of the redistillation product of the reaction product of Example I containing the compound having the structure:

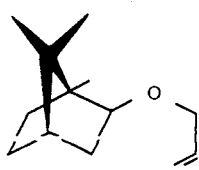

Figure 5:
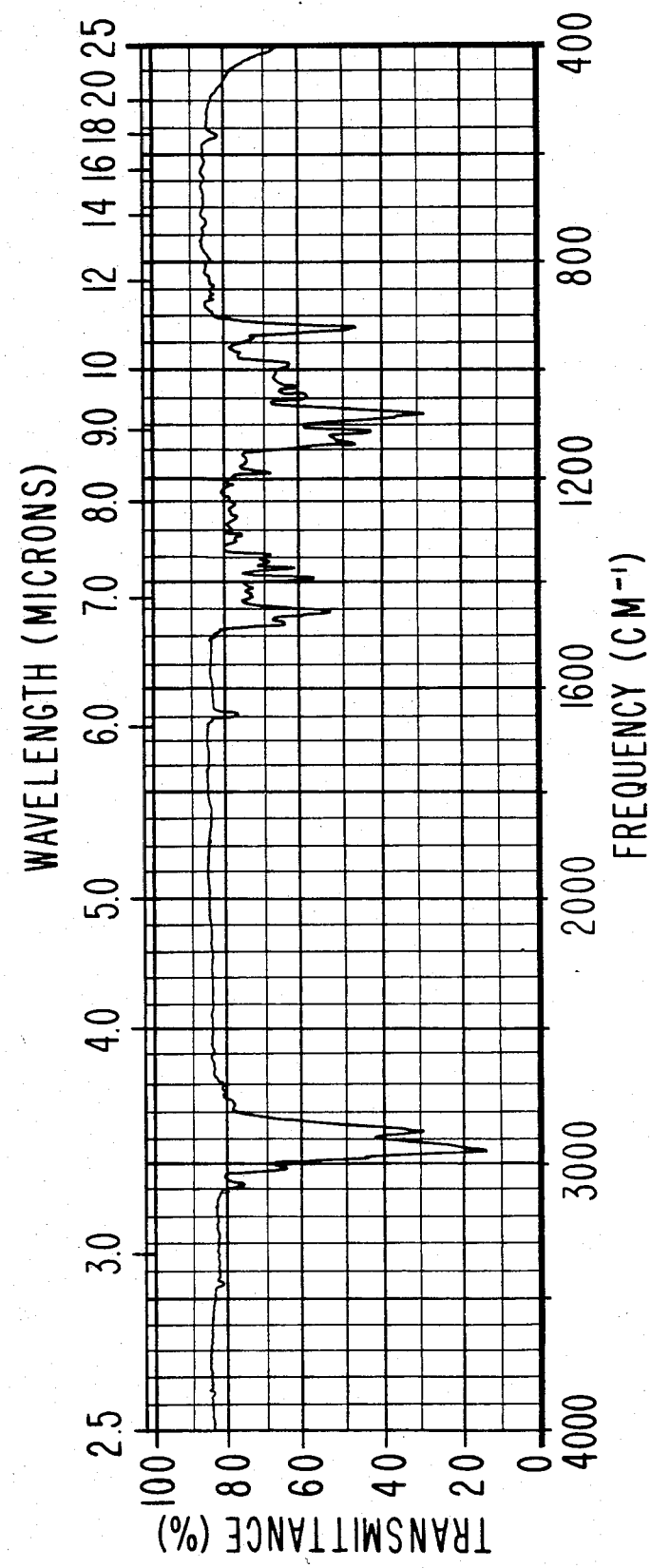

FIG. 5 is the infra-red spectrum for bulked fractions 2-7 of the redistillation product of the reaction product of Example I containing the compound having the structure:

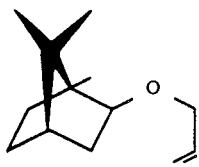

Figure 6:
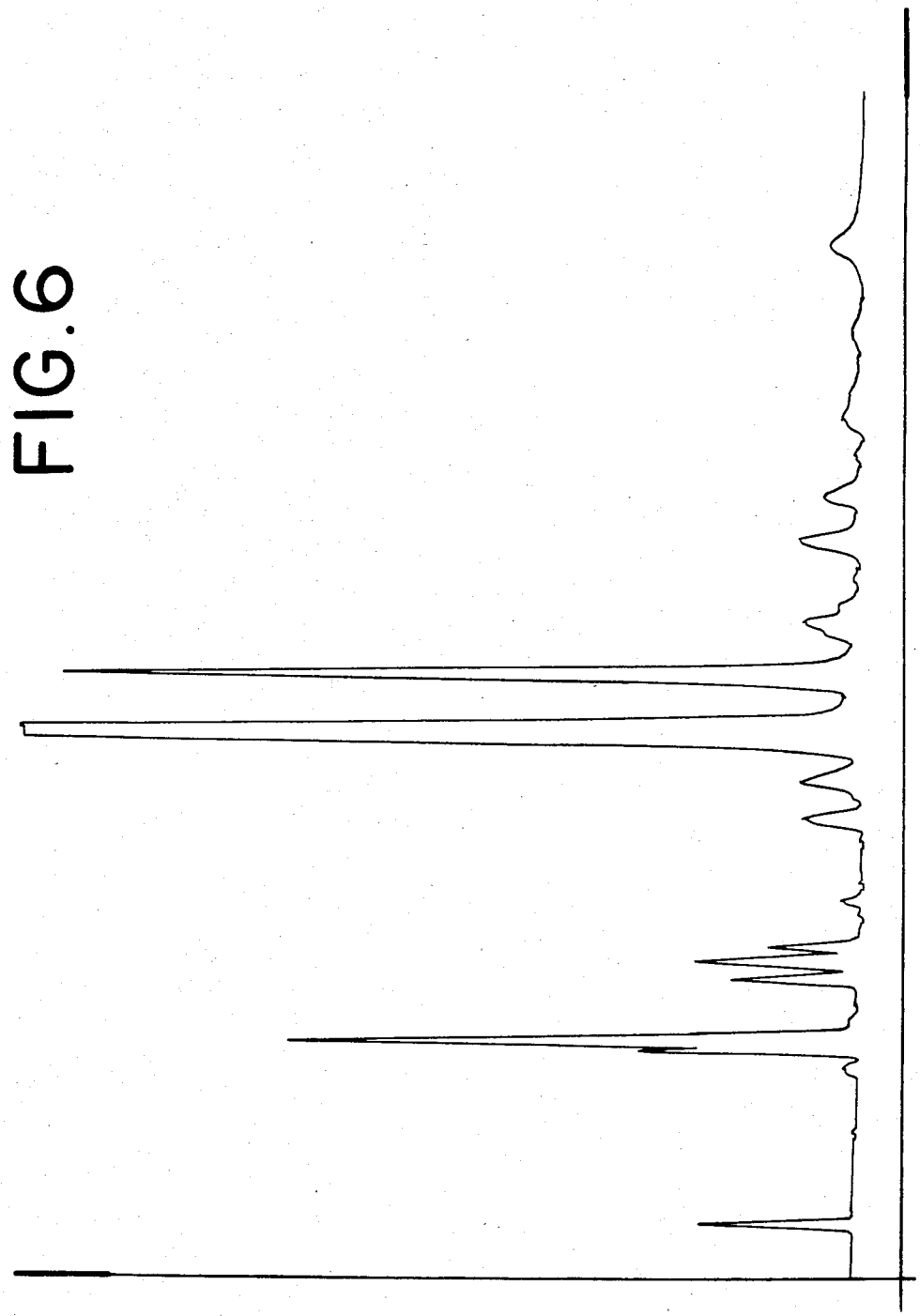

FIG. 6 is the GLC profile for the crude reaction product of Example II containing the compounds having the structures:

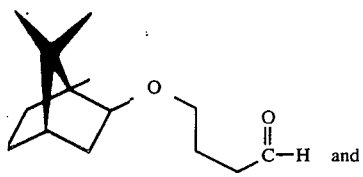

and

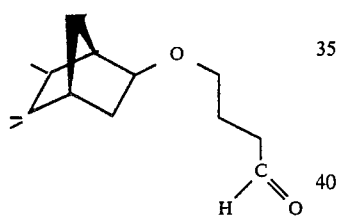

Figure 7:
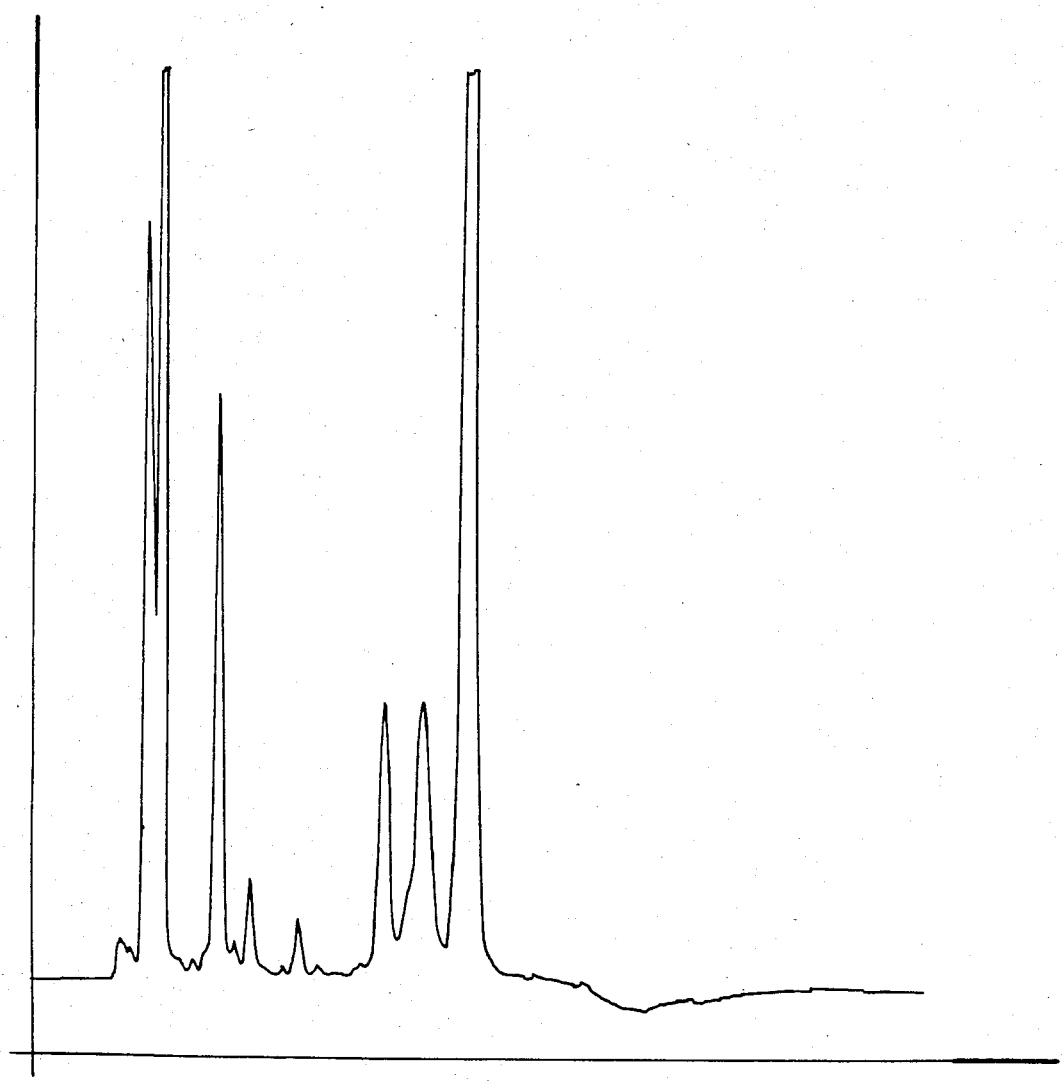

FIG. 7 is the GLC profile for fraction 1 of the distillation product of the reaction product of Example II containing the compound having the structure:

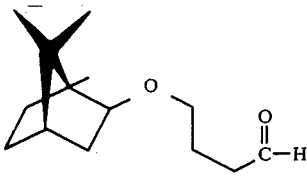

Figure 8:
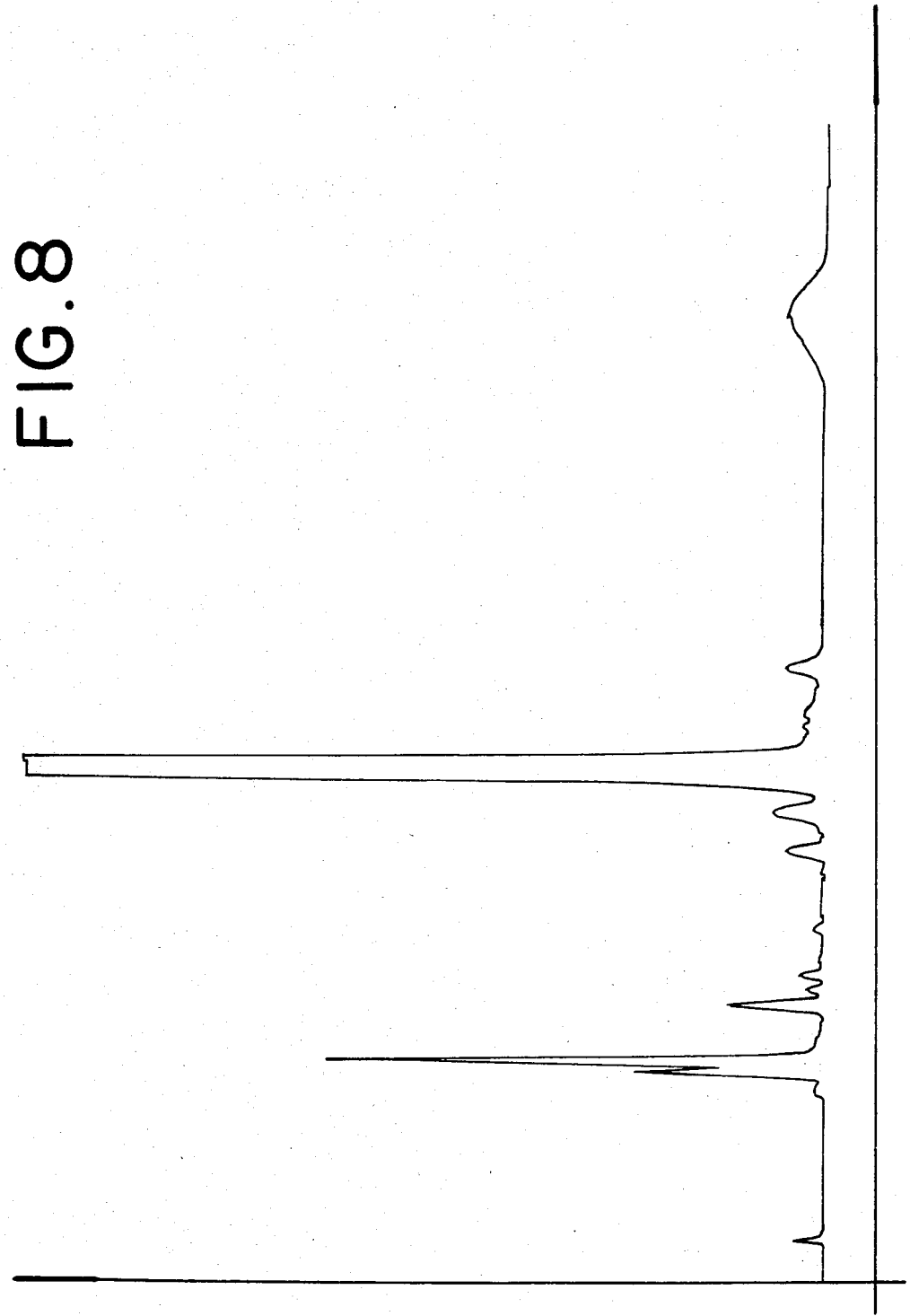

FIG. 8 is the GLC profile for fraction 2 of the distillation product of the reaction product of Example II containing the compound having the structure:

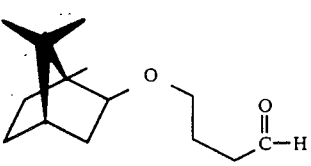

Figure 9:
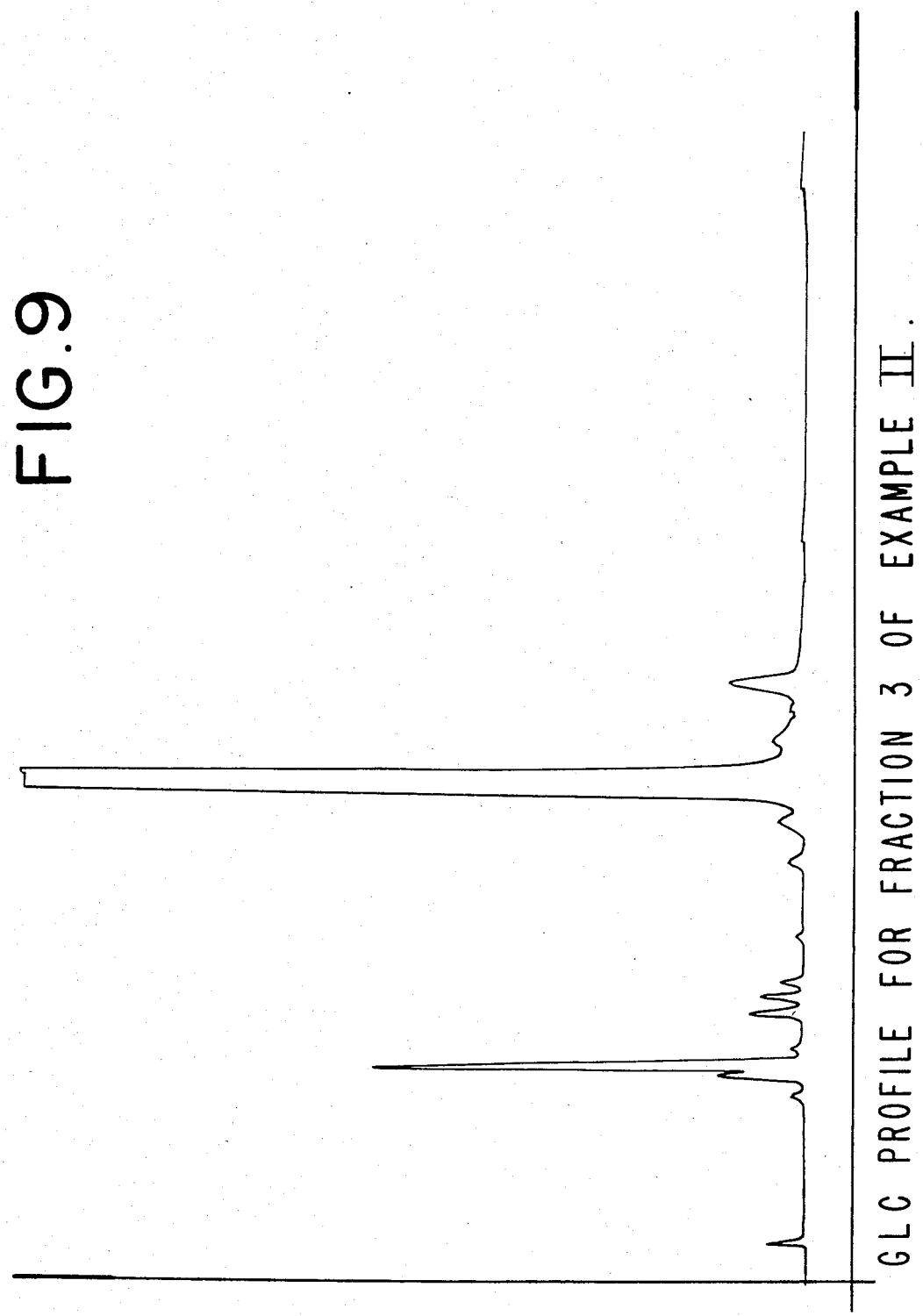

FIG. 9 is the GLC profile for fraction 3 of the distillation product of the reaction product of Example II containing the compound having the structure:

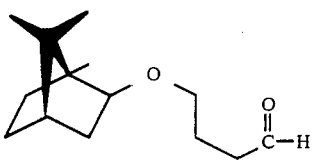

Figure 10:
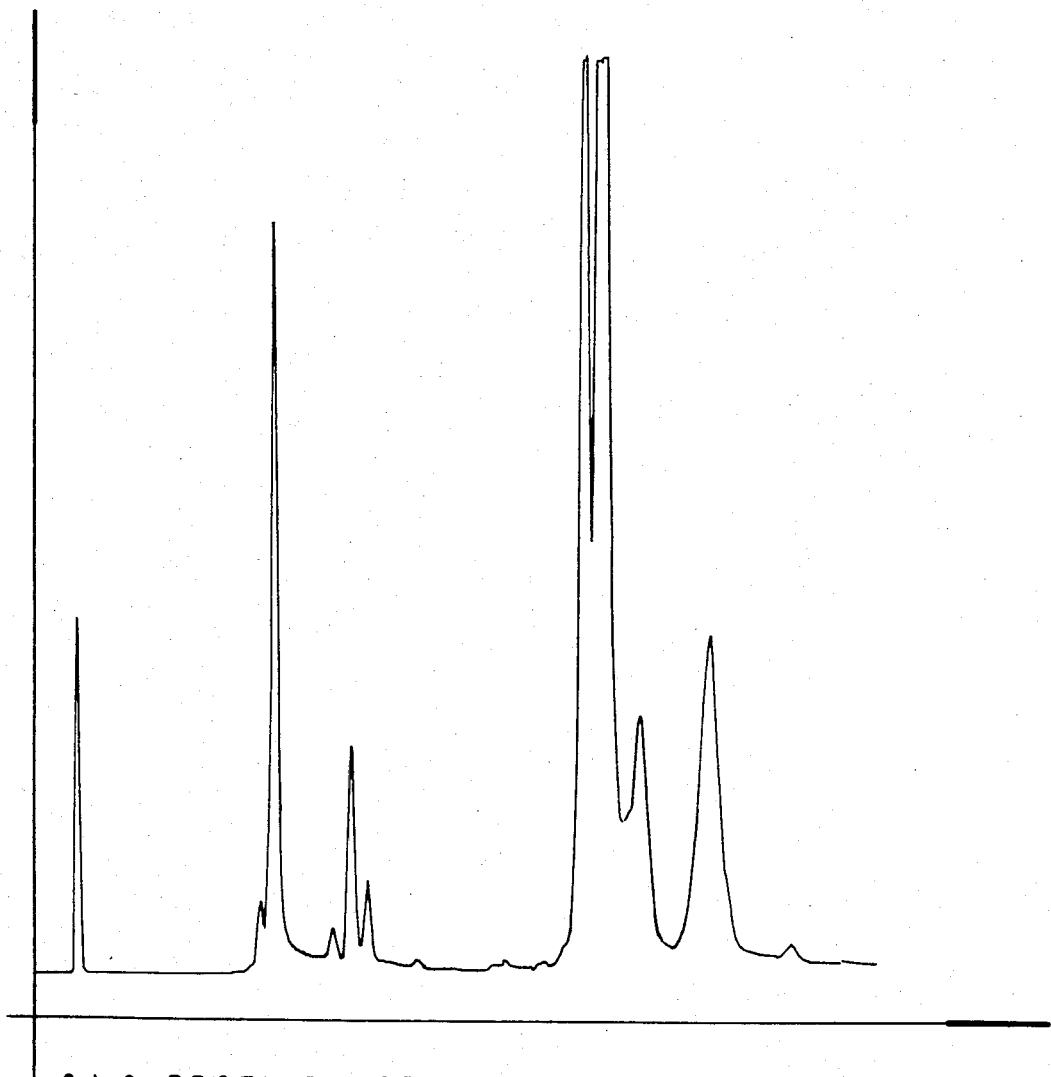

FIG. 10 is the GLC profile for fraction 4 of the distillation product of the reaction product of Example II containing the compound having the structure:

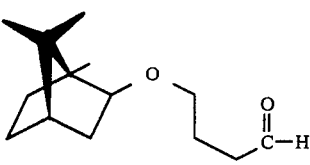

Figure 11:
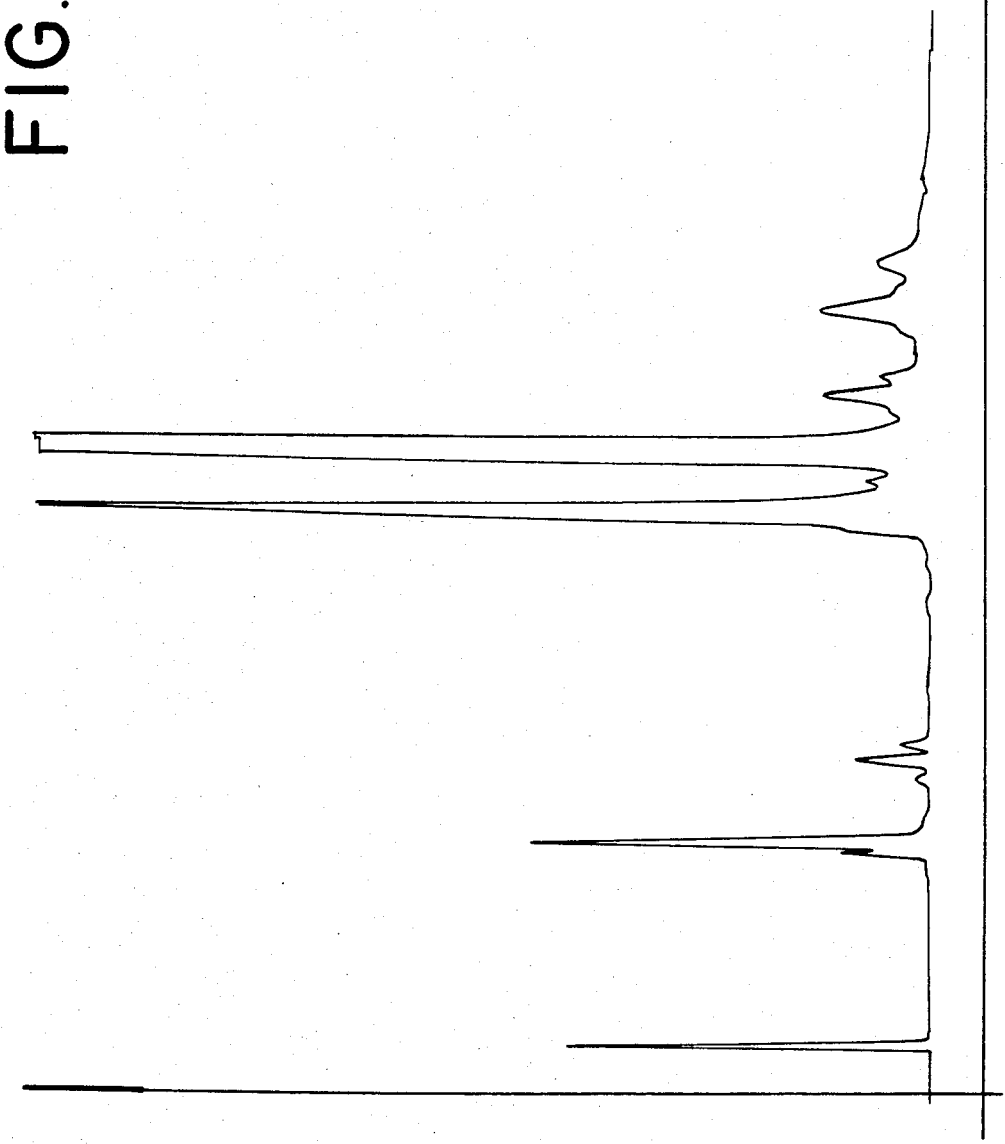

FIG. 11 is the GLC profile for fraction 5 of the distillation product of the reaction product of Example II containing the compound having the structure:

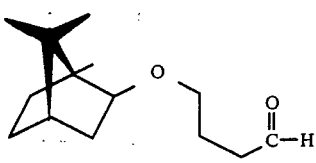

Figure 12:
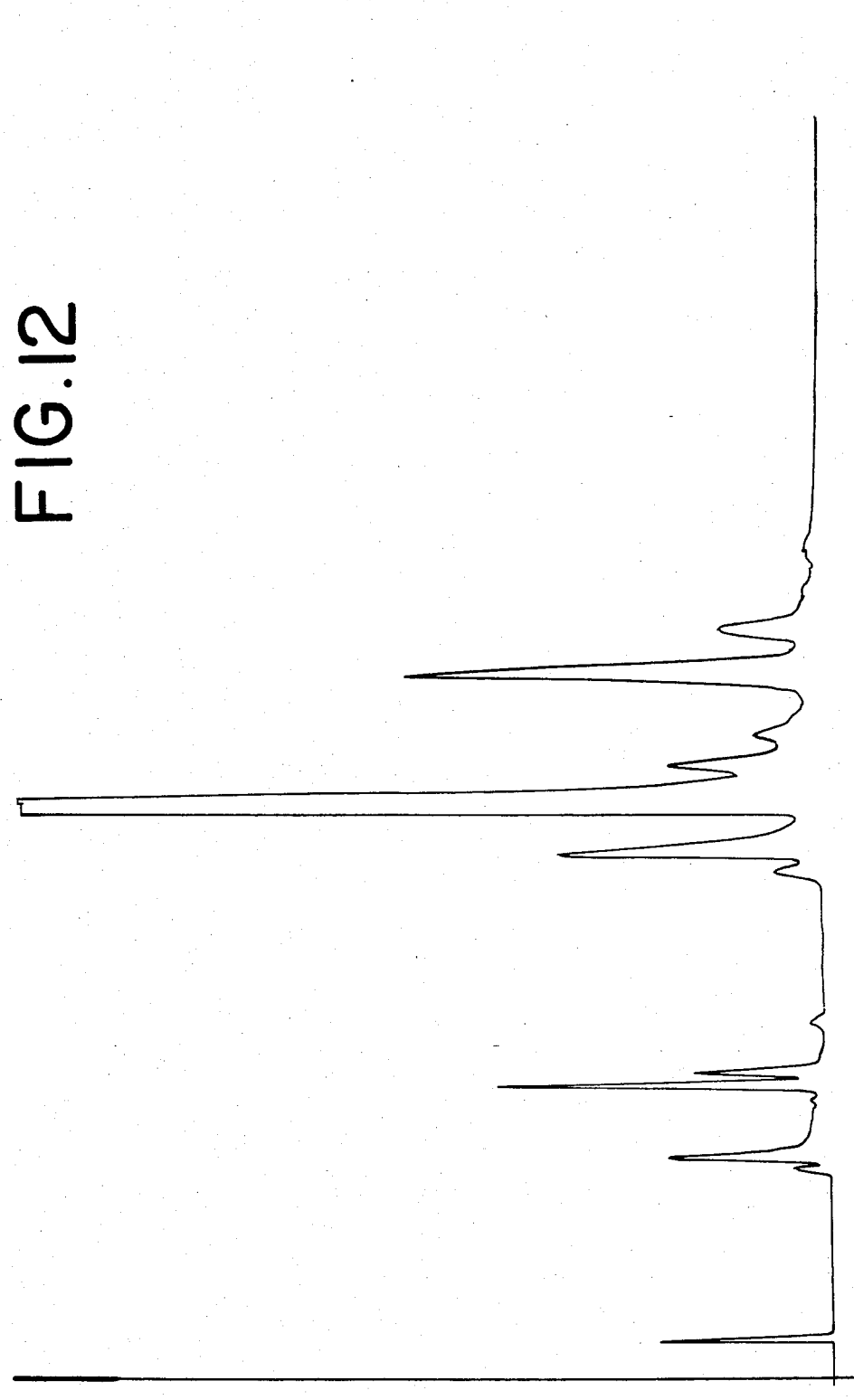

FIG. 12 is the GLC profile for fraction 6 of the distillation product of the reaction product of Example II containing the compound having the structure:

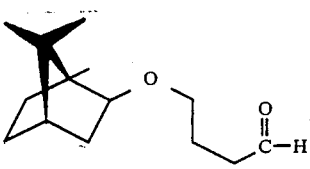

Figure 13:
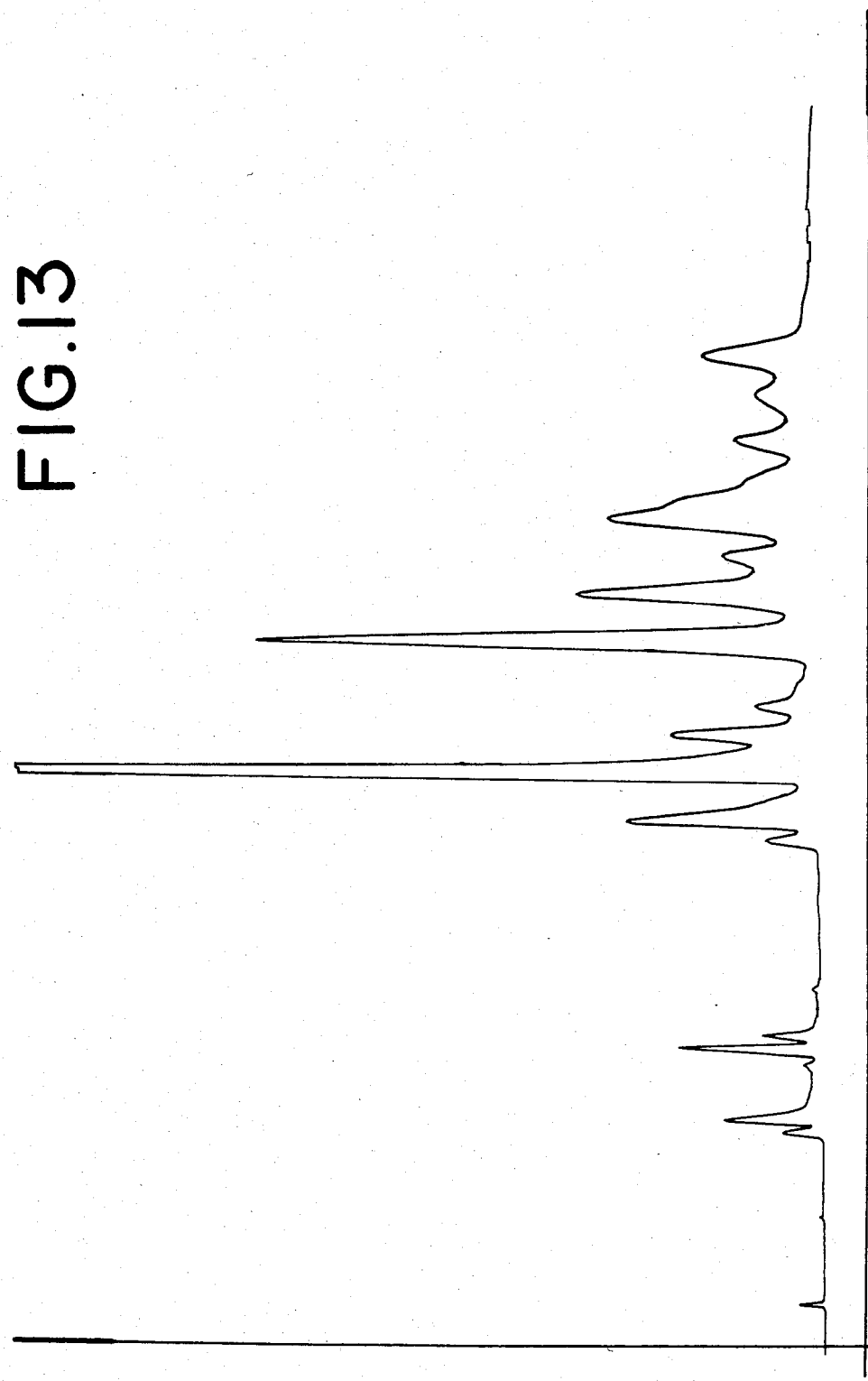

FIG. 13 is the GLC profile for fraction 7 of the distillation product of the reaction product of Example II containing the compound having the structure:

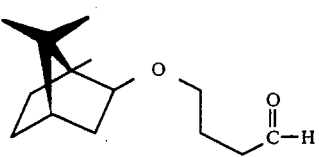

FIG. 14 is the NMR spectrum for fraction 5 of the distillation product of the reaction product of Example II which is the compound having the structure:

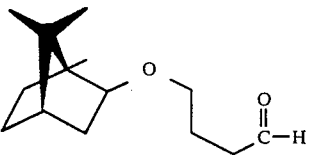

FIG. 15 is the infra-red spectrum for fraction 5 of the distillation product of the reaction product of Example II which is for the compound having the structure:

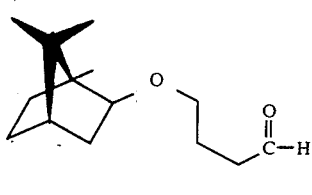

THE INVENTION

The present invention provides the family of hydrocarbyloxy alkanals defined according to the structure:

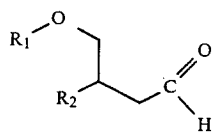

wherein $R_1$ is a moiety selected from the group consisting of:

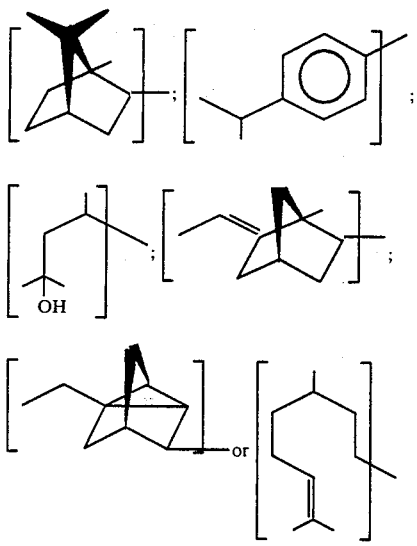

which are useful in augmenting or enhancing the aroma or taste of consumable materials including perfumes, perfumed articles and colognes. The present invention also provides methods for synthesizing such hydrocarbyloxy alkanals by reacting allylic alcohol defined according to the structure:

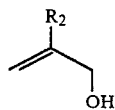

with a chemical compound having an electrophilic center which is a hydrocarbon or hydrocarbyl halide defined according to the structure:

wherein $R_1'$ is a saturated hydrocarbyl moiety or an unsaturated hydrocarbyl moiety and X is hydrogen or halogen; with the provisos that:
when X is halogen, $R_1'$ is saturated hydrocarbyl and when X is hydrogen, $R_1'$ is unsaturated hydrocarbyl;

and wherein $R_2$ represents hydrogen or methyl. The resulting compound formed has the structure:

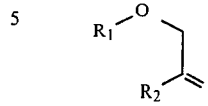

wherein $R_1$ and $R_2$ are defined supra. This compound is then reacted via an oxo reaction with carbon monoxide and hydrogen to form the hydrocarbyloxy alkanals defined according to the structure:

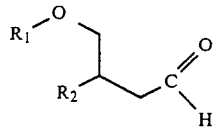

according to the reaction sequence:

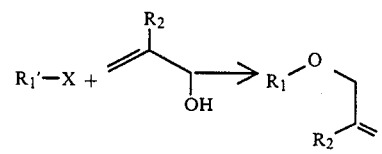

and

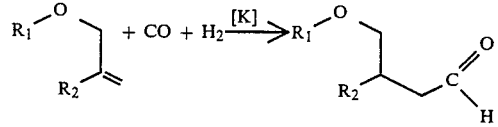

More specifically, our invention relates to the compound having the structure:

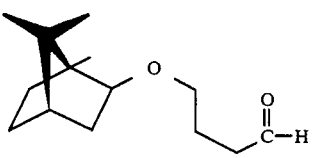

This compound of our invention produced according to the process of our invention is capable of augmenting, enhancing or providing natural pine, cypress-like and fir-balsam-like aroma nuances in perfume compositions, colognes and perfumed articles (e.g. perfumed polymers, solid or liquid anionic, cationic, nonionic or zwitterionic detergents, fabric softener articles, drier-added fabric softener articles, fabric softener compositions, cosmetic powders, hair preparations, shampoos and the like).

The compound having the structure:

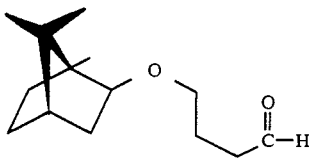

may exist in either the "exo" or "endo" form, that is, having the structures:

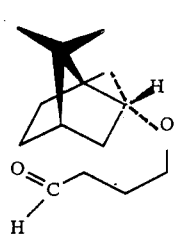 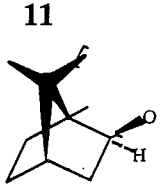 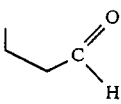

or the compound shown by the structure:

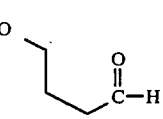

can represent mixtures of both compounds having the structures:

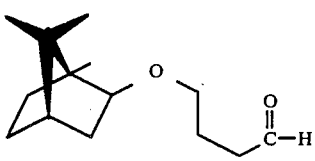

The compound of our invention is produced by first reacting allyl alcohol having the structure:

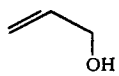

with camphene having the structure:

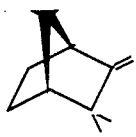

thereby producing a mixture of allyl ethers having the structures:

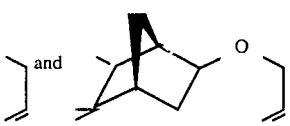

which mixture is primarily the compound having the structure:

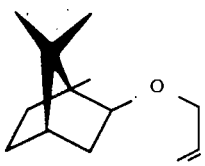

The mixture is fractionally distilled yielding substantially all compound having the structure:

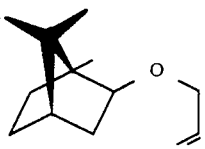

The compound having the structure:

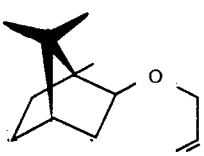

is then reacted via an oxo reaction with carbon monoxide and hydrogen to yield a mixture of compounds containing the compound having the structure:

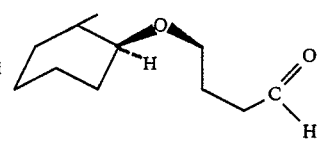

The reaction of the camphene with the allyl alcohol is shown thusly:

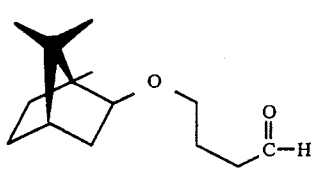

The reaction of the resulting allyl ether via the oxo reaction with carbon monoxide and hydrogen is shown thusly:

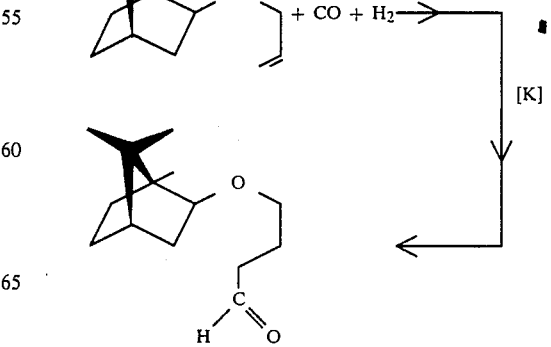

wherein the term [K] represents the oxo reaction catalyst.

The reaction of the allyl alcohol with the camphene takes place at a temperature in the range of from about 70° C. up to about 120° C. in the presence of a Lewis acid catalyst such as boron trifluoride etherate, stannic chloride, zinc chloride or aluminum chloride; preferably boron trifluoride etherate. The mole ratio of camphene:allyl alcohol may vary from about 0.5:1 up to about 1:0.5 with a preferred mole ratio of about 1:1.1 camphene:allyl alcohol (the allyl alcohol being in a slight molar excess). The amount of Lewis acid catalyst in the reaction mixture may vary from about 3 grams per liter of reaction mass up to about 15 grams per liter of reaction mass. The time of reaction may vary from about 2 hours up to about 15 hours; but when maintaining the temperature at about 80° C., the time of reaction is about 6 hours when using a boron trifluoride etherate catalyst.

At the end of this reaction, the reaction mass is worked-up by first neutralizing the acid catalyst, e.g. boron trifluoride etherate with an aqueous basic solution, e.g. aqueous sodium carbonate, then washing with water to neutral. The resulting product is then distilled and the distillation product (e.g. via fractional distillation) is used for the second reaction which involves the reaction of the compound having the structure:

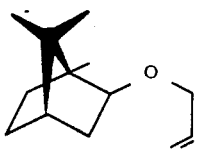

with a mixture of carbon monoxide and hydrogen via a "oxo" reaction.

The oxo reaction is carried out in the presence of a "oxo reaction catalyst" such as rhodium, $Co_2(CO)_8$, or an organophosphorous polydentate ligand such as those described in European Published Application No. 33,554 published on Aug. 12, 1981, the specification for which is incorporated herein by reference. Examples of which are:

$\phi_2-P-(CH_2)_2-P\phi_2$, $\phi-P+(CH_2)_2-P\phi_2]_2$, $P+(CH_2)_2-P\phi_2]_3$, $\phi_2P-HC=CH-P\phi_2$, and $\phi-P-CH-CH_2-P\phi_2$
       |
       $CH_3$ at pressures of from about 3 atmospheres up to about 1,000 atmospheres and at temperatures in the range of from about 30° C. up to about 150° C. Preferably when using a rhodium catalyst, the temperature of reaction is between 70° and 110° C.; when using a $Co_2(CO)_8$ catalyst, the temperature is between 110° and 120° C.; and when using a ligand such as those exemplified in European Published Application No. 33,554, the temperature may vary from 95° C. up to 120° C. as is set forth in the following table:

TABLE A

| Ligand | Reaction Temperature |
|---|---|
| $\phi_2P(CH_2)_2P\phi_2$ | 95–120° C. |

TABLE A-continued

| Ligand | Reaction Temperature |
|---|---|
| $\phi P\begin{smallmatrix}CH_2-CH_2-P\phi_2\\ \\CH_2-CH_2-P\phi_2\end{smallmatrix}$ | 120° C. |
| $P\begin{smallmatrix}CH_2-CH_2-P\phi_2\\CH_2-CH_2-P\phi_2\\CH_2-CH_2-P\phi_2\end{smallmatrix}$ | 120° C. |
| $\phi_2P-CH=CH-P\phi_2$ | 120° C. |
| $\phi_2P-CH-CH_2-P\phi_2$<br>     \|<br>     $CH_3$ | 95° C. |
| $\phi_2P(CH_2)_4P\phi_2$ | 95° C. |
| $\phi_2P(CH_2)_3P\phi_2$ | 95° C. |
| $P\phi_3$ | 120° C. |
| $\phi_2P(CH_2)_{10}P\phi_2$ | 120° C. |
| $\phi_2PCH_2P\phi_2$ | 120° C. |
| $(CH_3)_2P(CH_2)_2P(CH_3)_2$ | 120° C. |

The resulting reaction product is then separated as by fractional distillation thereby yielding a mixture of compounds including a major proportion of the compound having the structure:

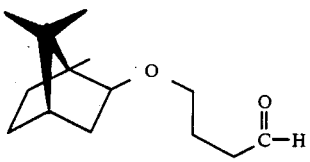

This compound may be further purified, if desired, by means of commercial chromatographic separation procedures. From a commercial standpoint, it is preferred not to carry out such a separation but to use the reaction mixture "as is" from the fractional distillation.

The aldehyde compound having the structure:

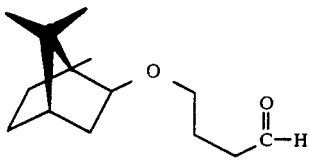

(hereinafter referred to as the "norbornyl oxybutyraldehyde") prepared in accordance with the process of our invention and one or more auxiliary perfume ingredients including, for example, alcohols, aldehydes other than the norbornyl oxybutyraldehyde of our invention, ketones, terpenic hydrocarbons, nitriles, esters, lactones, natural essential oils and synthetic essential oils, may be admixed so that the combined odors of the individual components produce a pleasant and desired fragrance particularly and preferably in the pine and lavender fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all states of evaporation and substances which retard evaporation; and (d) top notes which are usually low-boiling, fresh-smelling materials.

In perfume compositions, it is the individual components which contribute their particular olfactory characteristics, however, the overall sensory effect of the perfume composition will be at least the sum total of the effects of each of the ingredients. Thus, the norbornyl oxybutyraldehyde composition of matter prepared in accordance with the process of our invention can be used to alter, modify or enhance the aroma characteristics of a perfume composition, for example, by utilizing or moderating the olfactory reaction contributed by another ingredient or other ingredients in the composition.

The amount of norbornyl oxybutyraldehyde prepared in accordance with the process of our invention which will be effective in perfume compositions as well as in perfumed articles (e.g. perfumed polymers, anionic, nonionic, cationic or zwitterionic detergents, soaps, fabric softener compositions, fabric softener articles and hair preparations) and colognes depends upon many fabrics including the other ingredients, their amounts and the effects which are desired. It has been found that perfume compositions containing as little as 0.01% of the norbornyl oxybutyraldehyde composition prepared in accordance with the process of our invention or even less (e.g. 0.005%) can be used to impart a natural pine, cypress-like, fir-balsam-like aroma to soaps, cosmetics, anionic, cationic, nonionic or zwitterionic detergents, perfumed polymers, fabric softener compositions, fabric softener articles or other products. The amount employed can range up to 70% of the fragrance components and will depend on considerations of cost, nature of the end product, the effect desired on the finished product and the particular fragrance sought.

The norbornyl oxybutyraldehyde composition prepared in accordance with the process of our invention is useful (taken alone or taken together with other ingredients in perfume compositions) as an olfactory component in detergents and soaps, space odorants and deodorants, perfumes, colognes, toilet water, bath preparations such as creams, deodorants, hand lotions and sun screens; powders such as talcs, dusting powders, face powders, microporous "perfumed" slow release polymers, (e.g. polyurethane microporous polymers) and the like. When used as an olfactory component in perfumed articles, as little as 0.05% of the norbornyl oxybutyraldehyde prepared in accordance with the process of our invention will suffice to impart a natural pine, cypress-like, fir-balsam-like aroma to pine or lavender formulations. Generally no more than 6% of the norbornyl oxybutyraldehyde composition of our invention based on the ultimate end product is required in the perfumed article.

In addition, the perfume composition or fragrance composition of our invention can contain a vehicle or carrier for the norbornyl oxybutyraldehyde composition prepared in accordance with the process of our invention. The vehicle can be a liquid, such as a non-toxic alcohol (e.g. ethyl alcohol), a non-toxic glycol (e.g. 1,2-propylene glycol) or the like. The carrier can also be an absorbent solid such as a gum (e.g. gum arabic or xanthan gum) or components for encapsulating the composition (such as gelatin) as by coacervation or polymers such as urea formaldehyde polymers.

It will thus be apparent that the norbornyl oxybutyraldehyde prepared in accordance with the process of our invention can be utilized to alter, modify or enhance sensory properties, particularly organoleptic properties such as fragrances of a wide variety of consumable materials.

The following Examples I and II set forth a means for synthesizing the norbornyl oxybutyraldehyde of our invention. The examples following Example II serve to illustrate the organoleptic utilities of the norbornyl oxybutyraldehyde of our invention.

All parts and percentages given herein are by weight unless otherwise specified.

EXAMPLE I

Preparation of isobornyl allyl ether

Reaction:

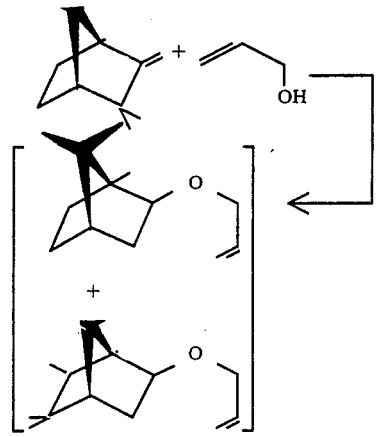

Into a 2 liter reaction flask equipped with stirrer, thermometer, reflux condenser and addition funnel is placed 201.6 grams of allyl alcohol and 8 grams of boron trifluoride diethyl etherate. The resulting mixture is heated to 80° C. and 680 grams of camphene (5.0 moles) and 100 grams of allyl alcohol in admixture are added to the reaction mass. The reaction mass is then stirred for a period of 6 hours while maintaining same at 80° C. At the end of the reaction, the reaction mass is washed with a sodium carbonate aqueous saturated solution until the pH is 9. The resulting product is then washed with water to neutral and distilled. The first fractional distillation yields the following fractions:

| Fraction Number | Vapor Temp (°C.) | Liquid Temp. (°C.) | Pressure mm/Hg | Weight of Fraction (grams) |
|---|---|---|---|---|
| 1 | 49 | 82 | 65 | |
| 2 | 64 | 89 | 12 | 41.1 |
| 3 | 100 | 105 | 12 | 160.8 |
| 4 | 107 | 112 | 12 | 192.3 |
| 5 | 109 | 113 | 12 | 199.8 |
| 6 | 109 | 114 | 12 | |
| 7 | 110 | 143 | 12 | |

Fractions 2-5 are bulked and redistilled yielding the following fractions:

| Fraction Number | Vapor Temp. (°C.) | Liquid Temp. (°C.) | Pressure mm/Hg |
|---|---|---|---|
| 1 | 63 | 93 | 35 |
| 2 | 65 | 106 | 35 |
| 3 | 70 | 109 | 25 |
| 4 | 68 | 106 | 23 |
| 5 | 98 | 99 | 16 |
| 6 | 99 | 100 | 17 |

-continued

| Fraction Number | Vapor Temp. (°C.) | Liquid Temp. (°C.) | Pressure mm/Hg |
|---|---|---|---|
| 7 | 99 | 100 | 17 |
| 8 | 95 | 95 | 12 |
| 9 | 95 | 95 | 11 |
| 10 | 96 | 96 | 12 |
| 11 | 94 | 96 | 12 |
| 12 | 94 | 100 | 12 |
| 13 | 96 | 210 | 12 |

Figure 1:
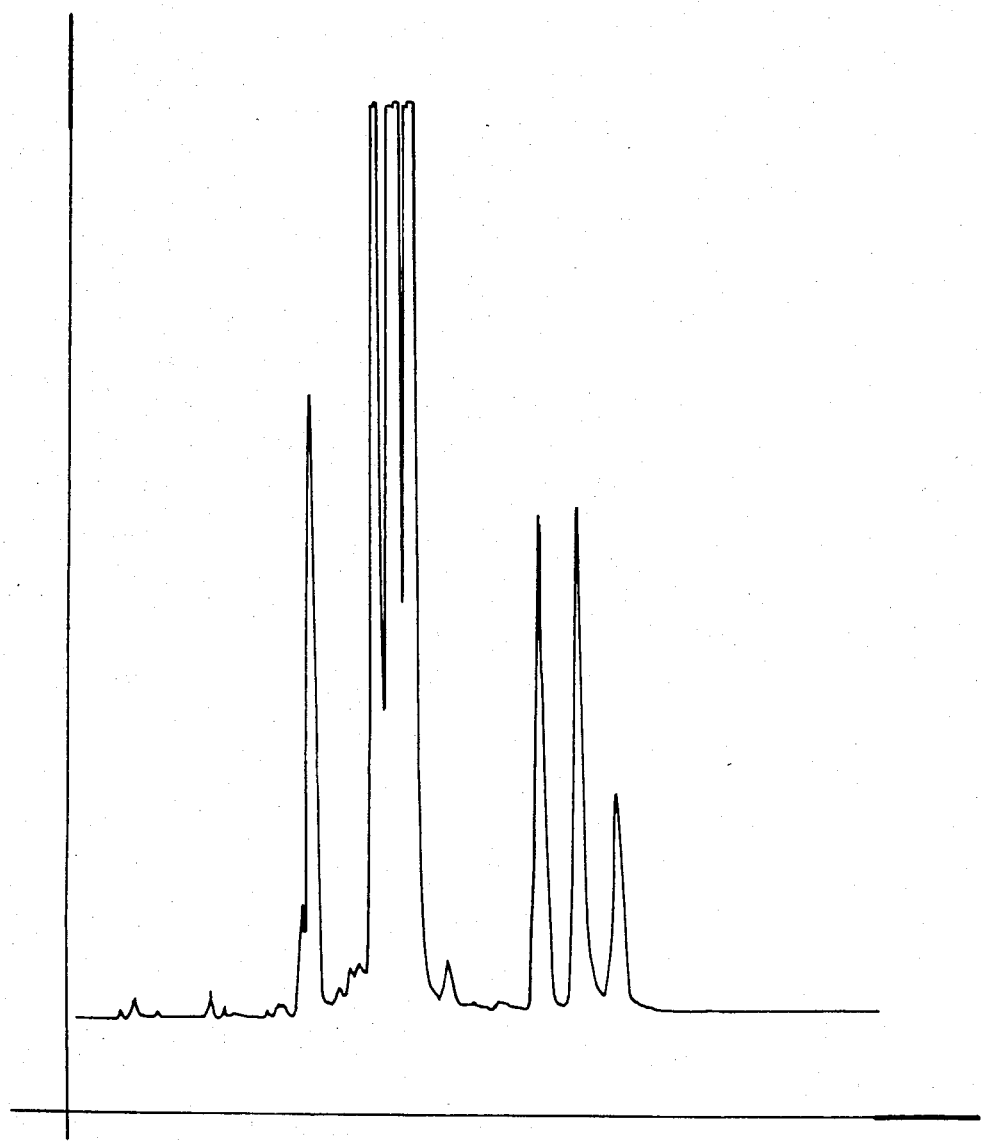
FIG. 1 is the GLC profile for the distillation product of the reaction product of Example I, first distillation, bulked fractions 1-7 (conditions: SE-30 column programmed at 150°-220° C. at 8° C. per minute). This reaction product contains the compounds having the structures.

FIG. 1 is the GLC profile for the first distillation product (bulked fractions 1-7). The conditions for the GLC are: SE-30 column programmed at 150°-220° C. at 8° C. per minute.

FIG. 2 is the GLC profile for fraction 7 of the first distillation.

FIG. 3 is the GLC profile for bulked fractions 1-7 of the second distillation.

FIG. 4 is the NMR spectrum for bulked fractions 1-7 of the second distillation which is substantially all compound having the structure:

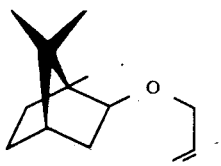

FIG. 5 is the infra-red spectrum for the bulked fractions 1-13 of the second distillation which is substantially all compound having the structure:

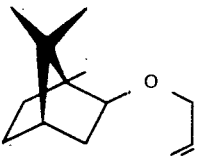

EXAMPLE II

Preparation of isobornyloxybutanal

Reaction:

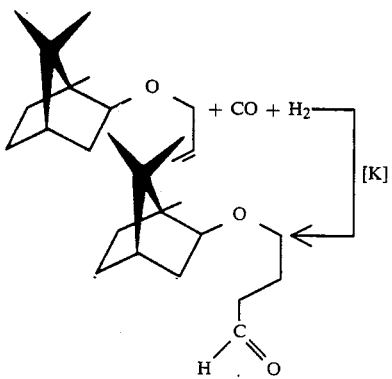

wherein K represents the catalyst having the structure:

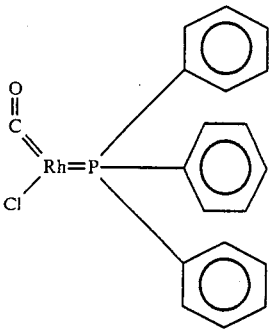

Into an autoclave rated for 1,000 psig pressure and containing heating elements is placed 194 grams (1 mole) of isobornyl allyl ether prepared according to Example I (bulked fractions 1-13); 2 grams of triphenyl phosphene; 0.2 grams of the compound having the structure:

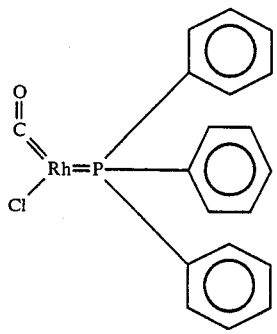

and 50 ml toluene. The autoclave is sealed and heated to 120° C. and pressurized to 500 psig. The temperature is raised to 200° C. and the pressure is raised to 700 psig using a 50:50 mole:mole mixture of carbon monoxide and hydrogen. The autoclave pressure is then maintained at 150°-200° C. and 500-700 psig for a period of 13 hours. At the end of the 13 hour period, the autoclave is depressurized, the contents are cooled and the autoclave is opened. The contents of the autoclave are then distilled first through a 12" Goodloe column and then redistilled through a spinning band column.

The fractions obtained from the 12" Goodloe column are as follows:

| Fraction Number | Vapor Temp. (°C.) | Liquid Temp. (°C.) | Pressure mm/Hg | Weight of Fraction (grams) |
|---|---|---|---|---|
| 1 | 119 | 165 | 4 | 13.9 |
| 2 | 125 | 175 | 3 | 16.1 |
| 3 | 150 | 244 | 3 | 17.7 |
| 4 | 195 | 264 | 3 | 13.0 |

The fractions obtained from the redistillation of all fractions from the Goodloe column distillation on the spinning band column are as follows:

| Fraction Number | Vapor Temp. (°C.) | Liquid Temp. (°C.) | Pressure mm/Hg | Weight of Fraction (grams) |
|---|---|---|---|---|
| 1 | 94 | 134 | 2.8 | 9.7 |
| 2 | 95 | 110 | 2.6 | 8.7 |

| Fraction Number | Vapor Temp. (°C.) | Liquid Temp. (°C.) | Pressure mm/Hg | Weight of Fraction (grams) |
|---|---|---|---|---|
| 3 | 62 | 147 | 2.6 | 3.5 |
| 4 | 102 | 163 | 2.4 | 2.8 |
| 5 | 114 | 178 | 2.4 | 3.3 |
| 6 | 70 | 194 | 2.8 | 5.9 |
| 7 | 64 | 240 | 2.9 | 4.4 |

FIG. 6 is the GLC profile for the crude reaction product of this example containing the compounds having the structures:

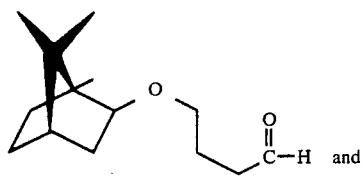

and

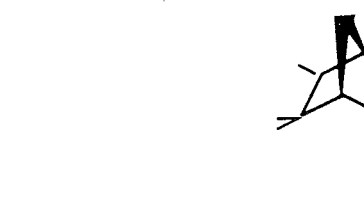

FIG. 7 is the GLC profile for fraction 1 of the distillation product of the reaction product of this example containing the compound having the structure:

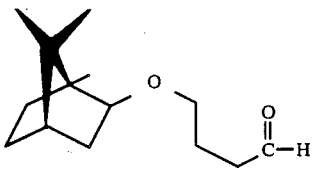

FIG. 8 is the GLC profile for fraction 2 of the distillation product of the reaction product of this example containing the compound having the structure:

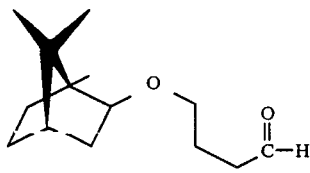

FIG. 9 is the GLC profile for fraction 3 of the distillation product of the reaction product of this example containing the compound having the structure:

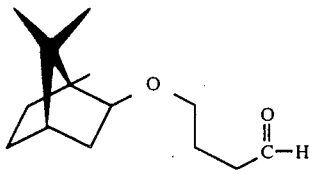

FIG. 10 is the GLC profile for fraction 4 of the distillation product of the reaction product of this example containing the compound having the structure:

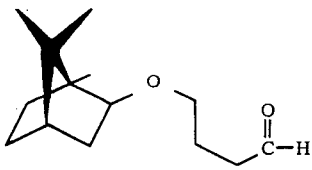

FIG. 11 is the GLC profile for fraction 5 of the distillation product of the reaction product of this example containing the compound having the structure:

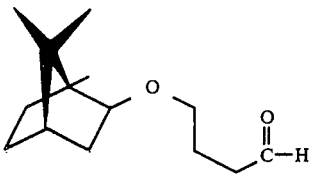

FIG. 12 is the GLC profile for fraction 6 of the distillation product of the reaction product of this example containing the compound having the structure:

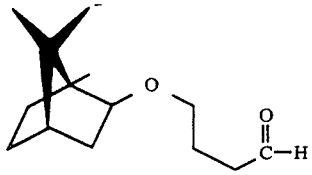

FIG. 13 is the GLC profile for fraction 7 of the distillation product of the reaction product of this example containing the compound having the structure:

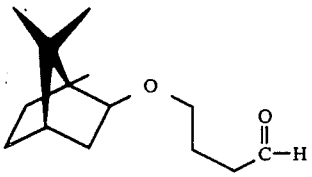

FIG. 14 is the NMR spectrum for fraction 5 of the distillation product of the reaction product of this example which is the compound having the structure:

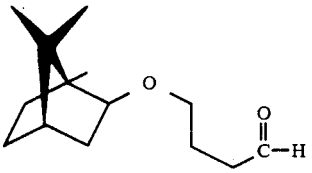

FIG. 15 is the infra-red spectrum for fraction 5 of the distillation product of the reaction product of this example which is for the compound having the structure:

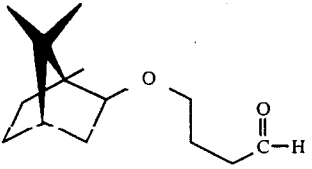

EXAMPLE III

Pine fragrance

The following pine fragrance formulation is prepared:

| Ingredients | Parts by Weight |
| --- | --- |
| Isobornyl acetate | 100 |
| Camphor | 10 |
| Terpineol | 25 |
| Fir balsam absolute | 20 |
| (50% in diethyl phthalate) | |
| Coumarin | 4 |
| Linalool | 30 |
| Fenchyl alcohol | 10 |
| Anethol | 12 |
| Lemon terpenes washed | 50 |
| Borneol | 5 |
| Galbanum oil | 5 |
| Turpentine Russian | 150 |
| Eucalyptol | 50 |
| 2,2,6-trimethyl-1-cyclohexene-1-carboxaldehyde | 12 |
| Maltol (1% in diethyl phthalate | 5 |
| Bulked fractions 3-5 of the final distillation product of Example II consisting essentially of the compound having the structure: 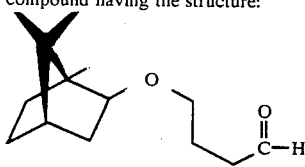 | 28 |

The norbornyl oxybutyraldehyde prepared according to Example II imparts to the pine formulation an intense natural pine, cypress-like and fir balsam-like aroma profile. The pine formulation with the additional intense nuances caused by the use of the product of Example II has advantageous and unexpected properties in the perfume industry.

EXAMPLE IV

Preparation of cosmetic powder compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
| --- | --- |
| The compound having the structure: (bulked fractions 3-5 of the distillation product of the reaction product of Example II). | A natural pine, cypress-like, fir balsam-like aroma profile. |
| Perfume composition produced according to Example II. | A natural piney aroma with cypress and fir balsam-like undertones. |

EXAMPLE V

Perfumed liquid detergents

Concentrated liquid detergents (lysine salt of n-dodecylbenzene sulfonic acid as more specifically described in U.S. Pat. No. 3,948,818, issued on Apr. 6, 1976 incorporated by reference herein) with aroma nuances as set forth in Table I of Example IV are prepared containing 0.10%, 0.15%, 0.20%, 0.25%, 0.30% and 0.35% of the substance set forth in Table I of Example IV. They are prepared by adding and homogeneously mixing the appropriate quantity of substance set forth in Table I of Example IV in the liquid detergent. The detergents all possess excellent aromas as set forth in Table I of Example IV, the intensity increasing with greater concentrations of substance as set forth in Table I of Example IV.

EXAMPLE VI

Preparation of colognes and handkerchief perfumes

Compositions as set forth in Table I of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example IV are imparted to the colognes and to the handkerchief perfumes at all levels indicated.

EXAMPLE VII

Preparation of soap compositions

One hundred grams of soap chips (per sample) (IVORY ®, produced by the Procter & Gamble Company of Cincinnati, Ohio), are each mixed with one gram samples of substances as set forth in Table I of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example IV.

EXAMPLE VIII

Preparation of solid detergent compositions

Detergents are prepared using the following ingredients according to Example I of Canadian Pat. No. 1,007,948 (incorporated herein by reference):

| Ingredient | Percent by Weight |
| --- | --- |
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table I of Example IV. Each of the detergent samples has an excellent aroma as indicated in Table I of Example IV.

EXAMPLE IX

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:
 1. A water "dissolvable" paper ("Dissolvo Paper")
 2. Adogen 448 (m.p. about 140° F.) as the substrate coating; and 3. An outer coating having the following formulation (m.p. about 150° F.):
   57% $C_{20-22}$ HAPS
   22% isopropyl alcohol
   20% antistatic agent
   1% of one of the substances as set forth in Table I of Example IV.

Fabric softening compositions prepared according to Example I at column 15 of U.S. Pat. No. 3,632,396 having aroma characteristics as set forth in Table I of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table I of Example IV, supra.

EXAMPLE X

Hair spray formulations

The following hair spray formulation is prepared by first dissolving PVP/VA E-735 copolymer manufactured by the GAF Corporation of 140 West 51st Street, New York, N.Y. in 91.62 grams of 95% food grade ethanol. Eight grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example IV | 0.10 weight percent |

The perfuming substances as set forth in Table I of Example IV add aroma characteristics as set forth in Table I of Example IV which are rather intense and aesthetically pleasing to the users of the soft-feel, good-hold pump hair sprays.

EXAMPLE XI

Conditioning shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

Gafquat ®755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting Composition A and Composition B are then mixed in a 50:50 weight ratio of A:B and cooled to 45° C. and 0.3 weight percent of perfuming substance as set forth in Table I of Example IV is added to the mixture. The resulting mixture is cooled to 40° C. and blending is carried out for an additional one hour in each case. At the end of this blending period, the resulting material has a pleasant fragrance as indicated in Table I of Example IV.

PATENTS INCORPORATED HEREIN BY REFERENCE

The following patents referred to supra are hereby incorporated herein by reference:
U.S. Pat. No. 3,632,396
U.S. Pat. No. 3,948,818
Canadian Pat. No. 1,007,948

What is claimed is:

1. A product containing norbornyl oxybutyraldehyde having the structure:

produced according to the process comprising the steps of:
(i) reacting allyl alcohol with camphene in order to form isobornyl allyl ether defined according to the structure:

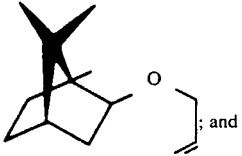; and (ii) reacting the resulting isobornyl allyl ether with a mixture of carbon monoxide and hydrogen under superatmospheric pressure in the presence of an oxo reaction catalyst.

* * * * *